United States Patent [19]

Metz et al.

[11] Patent Number: 4,960,793

[45] Date of Patent: Oct. 2, 1990

[54] DIETHYLENE GLYCOL MONOESTER DERIVATIVES, COMPOSITIONS AND THERAPEUTIC USE

[75] Inventors: Gunter Metz, Blaubeuren; Kurt Rauchle, Blaubeuren-Sonderbuch; Manfred Erdmann, Neu-Ulm, all of Fed. Rep. of Germany

[73] Assignee: Merckle GmbH, Blaubeuren, Fed. Rep. of Germany

[21] Appl. No.: 331,124

[22] Filed: Mar. 31, 1989

[51] Int. Cl.$^5$ .................... A61K 31/25; C07C 69/614
[52] U.S. Cl. ...................................... 514/532; 560/102
[58] Field of Search ......................... 560/102; 514/532

[56] References Cited

U.S. PATENT DOCUMENTS 4,699,925  10/1987  Uchida et al. ...................... 560/102

FOREIGN PATENT DOCUMENTS 728642  4/1955  United Kingdom .

Primary Examiner—Robert W. Ramsuer
Attorney, Agent, or Firm—Venable, Baetjer, Howard & Civiletti

[57] ABSTRACT

Novel diethylene glycol monoester of antirheumatically effective acids, e.g., lonazolac and diclofenac and others are disclosed which have inflammation inhibitory properties superior to the corresponding acid base forms. They may be produced through direct esterification without elimination of water and are suitable in the fight against diseases of the rheumatic complex.

7 Claims, No Drawings

DIETHYLENE GLYCOL MONOESTER DERIVATIVES, COMPOSITIONS AND THERAPEUTIC USE

The present invention relates to diethylene glycol monoesters of antirheumatically effective acids of the group consisting of
(a) 3-(4-chlorophenyl)-phenyl-1H-pyrazole-4-acetic acid (lonazolac)
(b) 2-[(2,6-dichlorophenyl)amino]-phenyl acetic acid (diclofenac)
(c) 2-(2-fluoro-4-biphenyl-propionic acetic acid (flurbiprofen)
(d) 2-(4-isobutylphenyl)-propionic acid (ibuprofen)
(e) 2-(3-benzoylphenyl)-propionic acid (ketoprofen).

In addition to the racemic compounds of the acids of (c) to (e), the optically active, dextro- and levorotatory isomers are also included within the scope of the invention.

The production of diethylene glycol monoester of flufenamic acid by conversion of 2-(2-chloroethoxyethanol with the potassium salt of flufenamic acid is well known (West German patent DE-PS 19 39 112). It is also well known that by using acidic catalysis and removal of the reaction water at higher temperatures (100° C. to 180° C.) flufenamic acid may be directly converted with 2-(2-hydroxyethoxy)ethanol to produce the diethylene glycol monoester (West German patent DE-PS 28 34 167). Alternatively, it may be obtained under basic conditions by transesterification of low weight molecular ester with diethylene glycol (West German patent DE-PS 28 34 168). Both of these methods are also suitable for the production of diethylene glycol monoesters of the acids (a) to (e). For diclofenac the reaction temperature must be kept under 140° C. because of its pronounced tendency of forming ring closures. A particularly gentle method of producing purified ester, which also in the case of acids (a) to (e) provided yields of 60–75%, is the direct conversion with carbonyl dimidazol at room temperature. However, due to its cost, this method is not practical.

It was surprisingly found that esterification of the acids (a) to (e) may be accomplished using acidic catalysis without removal of the reaction water at slightly elevated, i.e., median or intermediate, temperatures and with shorter reaction times, when 8 to 15 mol of diethylene glycol, preferably 10.5 to 12 mol, is used per mol of acid. Suitable acidic catalysts are Lewis acids, zinc chloride, sulfuric acid, phosphoric acid, polyphosphoric acid, benzol sulfonic acid, p-toluol sulfonic acid or mixtures of phosphoric acid and p-toluol sulfonic acid, at molecular conditions of 0.1 to 1.0 mol catalyst for each mol acid. The reaction temperature is 60° C. to 120° C., preferably 80° to 100° C. with reaction times of 1 to 5 hours.

It is particularly surprising that the remaining reaction water in the residue allows for such a high ester yield, since according to prior art, e.g., West German patent No. 28 34 167, a shift of the reaction equilibrium in the favor of ester requires the removal of the reaction water, i.e., azeotropical elimination.

After the reaction the excess diethylene glycol is removed (A) by distillation after neutralization, if necessary, by addition of alkali or alkaline earth hydroxides or carbonates in solid form or (B) by adding water, thus precipitating crude ester, or obtaining it through suitable solvents. The obtained crude ester is either distilled in a two-phase high vacuum distillation facility or cleaned by using preparative median-pressure fluid chromatography over usual sorbents, preferably silica gel. Pressures of 10–20 bar are suitable.

The diethylene glycol monoester according to the invention has inflammation inhibitory properties. It may be used in medicinal drugs with concentration and the dosage corresponding to those of the well known acid base forms.

The inflammation inhibitory properties of the new ester was compared to the various standards by using a paw edema test on rats. Through oral administration the animals (n=5 per group) received the substance one hour prior to intraplantar injection of carrageenin (1% suspension, 0.1 ml). The substance effect was determined three hours after the injection. For dermal application the animals (n=10 per group) received the substance dissolved in a constant volume of a compatible organic solvent. The solution was applied on the same paw 0.5 hours prior and 2.5 hours after intraplantar injection of kaolin (10% suspension, 0.1 ml). The measured value was determined four hours after the injection. The inhibitory effect relates to the corresponding value of the untreated control group, who each received the vehicle. The results are summarized in Table 1.

TABLE 1

| Substance | oral administration | | dermal application | |
|---|---|---|---|---|
| | Dose mg/kg | % Inhibition | Dose mg/kg | % Inhibition |
| Diclofenac | 100 | 38 | 10 | 36 |
| Diclofenac ester | 50 | 39 | 13* | 47 |
| Flurbiprofen | 50 | 40 | 10 | 28 |
| Flurbiprofen ester | 10 | 38 | 13.6* | 41 |
| Ibuprofen | 100 | 41 | 10 | 9 |
| Ibuprofen ester | 50 | 42 | 14.3* | 45 |
| Ketoprofen | 5 | 38 | 10 | 33 |
| Ketoprofen ester | 2.5 | 36 | 13.5* | 45 |
| Lonazolac | 25 | 38 | 10 | 3 |
| Lonazolac ester | 25 | 49 | 12.8* | 26 |

*The dosage corresponds to 10 mg/kg of the standard

As the results show the new ester is superior to the corresponding acids as the standard. Compared to the standard the same inhibitory effect is obtained after oral administration with a substantially reduced ester dose or a higher inhibitory effect is obtained at an equivalent dose (lonazolac). With dermal application, during the time of measurement, the ester is pronounced superior at equimolar dosage.

The ester according to the invention is use in pharmaceutical preparations for dermal application in concentrations of 1 to 20 weight percent, preferably 5 to 10 weight percent. Suitable as dermal formulations are salves and cremes of the type oil in water (O/W) or water in oil (W/O) by using usual ointment basis and auxiliary adjuvants, such as fatty components, emulsifiers and stabilizers. Further, gels can be prepared using Tylose, carboxymethylcellulose, salts of acrylic acid polymers or acrylic acid-acrylamide copolymers as structure builders in aqueous or alcoholic-aqueous preparation forms, and solutions are prepared in dermal compatible solvents, such as alcohol, alcohol water mixtures or fatty alcohols and esters.

Equally suitable are dermal formulations that in addition contain penetration agents, e.g., dimethylsulfoxid in concentrations of 10 to 40 weight percentage or urea with 5 to 10 weight percentage.

The pharmaceutical preparations produced in this fashion, particularly for dermal application, are used to combat diseases of the rheumatic complex. Here the diethylene glycol monoester of lonazolac and diclofenac are especially preferred.

EXAMPLE 1

2-(2-hydroxyethoxy-ethyl-[2-(2,6-dichloroanilino)-phenyl-acetate]

291 g (1 mol) Diclofenac was suspended in 1110 g (10.5 mol) diethylene glycol and after adding 17.5 g (0.9 mol) p-toluol sulfonic acid monohydrate and 13.4 g (0.115 mol) o-phosphoric acid was heated at 80° C. for one hour with stirring. After cooling off, the mixture was neutralized using a solution of 35 g sodium carbonate in one liter of water. The precipitated crude ester was twice extracted with 250 ml chloroform. The chloroform phase was washed with water, dried over sodium sulphate and evaporated. The residue was cleaned with a mixture of acetic ester and light petroleum (2:3, v:v) as solvent over silica gel 60 using median pressure fluid chromatography. After evaporation of the solvent 280 g (72%) of a slightly yellowish oil was obtained.

EXAMPLE 2

2-(2-hydroxyethoxy)ethyl-[3-(4-chlorophenyl)-1-phenyl-1H-pyrazole-4-acetate]

313 g (1 mol) lonazolac was added to a solution of 30 g (0.25 mol) concentrated sulfuric acid in 1110 g (10.5 mol) diethylene glycol and heated for two hours at 80° C. After cooling off, 4.5 liter of 5% sodium carbonate solution was added by stirring and the mixture extracted with 2×250 ml chloroform. The washed and dried chloroform solution was evaporated. The obtained crude ester was distilled in a high vacuum distillation facility at 210° C./0.8 Pa, thereby obtaining 265 g (65%) of purified ester.

Additional diethylene glycol monoester derivatives were prepared using 1 mol acid and 10.5 mol diethylene glycol as set forth in Table 2.

TABLE 2

| Acid | Catalyst (mol) | reaction time (hr.) | reaction temp. (°C.) | Purific. | °C./Pa | final yield (%) |
|---|---|---|---|---|---|---|
| Lonazolac | p-toluol sulfonic acid (0.9) + o-phosphoric acid (0.115) | 3 | 80 | distill. | 210/0.8 | 76 |
| Lonazolac | o-phosphoric acid (0.115) | 4 | 120 | MFC* | — | 67 |
| Ketoprofen | p-toluol sulfonic acid (0.9) + o-phosphoric acid (0.1) | 3 | 80 | distill. | 170/1.06 | 70 |
| Flurbiprofen | p-toluol sulfonic acid (0.1) | 2 | 80 | distill. | 180/1.33 | 64 |
| Ibuprofen | p-toluol sulfonic acid | 3 | 80 | distill. | 140/3.99 | 71 |
| (+)-Ibuprofen | p-toluol sulfonic acid | 3 | 80 | distill. | 140/3.99 | 69[1] |
| (−)-Ibuprofen | p-toluol sulfonic acid | 3 | 80 | MFC* | — | 72[2] |
| Diclofenac | polyphosphoric acid (26 g) + p-toluol sulfonic acid (0.18) | 1 | 80 | MFC* | — | 66 |

*median pressure fluid chromatography corresponding to example 1.
[1] $\alpha 20_D = +45°$
[2] $\alpha 20_D = -35°$

What is claimed is:

1. A diethylene glycol monoester of the antirheumatically effective acids of flurbiprofen, and the optically active isomers thereof.

2. A pharmaceutical composition comprising an anti-inflammatory effective amount of the diethylene glycol monoester of claim 1 and a pharmaceutically acceptable carrier.

3. The pharmaceutical composition of claim 2, which contains about 1%–20% of said monoester.

4. The pharmaceutical composition of claim 2 which contains about 5%–10% of said monoester.

5. The pharmaceutical composition of claim 2 suitable for dermal application which further comprises about 10% to about 40% dimethylsulfoxide.

6. The pharmaceutical composition of claim 5 which further comprises about 5% to about 10% urea.

7. A method for treating diseases of the rheumatic complex which comprises administering the pharmaceutical composition of claim 2.

* * * * *